(12) United States Patent
Smith, III et al.

(10) Patent No.: US 10,077,278 B2
(45) Date of Patent: Sep. 18, 2018

(54) SYNTHETIC METHODS FOR DIBORON REAGENTS AND RELATED COMPOUNDS

(71) Applicant: BOARD OF TRUSTEES OF MICHIGAN STATE UNIVERSITY, East Lansing, MI (US)

(72) Inventors: Milton R. Smith, III, East Lansing, MI (US); Robert E. Maleczka, Jr., Dewitt, MI (US)

(73) Assignee: BOARD OF TRUSTEES OF MICHIGAN STATE UNIVERSITY, East Lansing, MI (US)

( * ) Notice: Subject to any disclaimer, the term of this patent is extended or adjusted under 35 U.S.C. 154(b) by 0 days.

(21) Appl. No.: 14/868,557

(22) Filed: Sep. 29, 2015

(65) Prior Publication Data

US 2016/0090390 A1    Mar. 31, 2016

Related U.S. Application Data

(60) Provisional application No. 62/057,780, filed on Sep. 30, 2014.

(51) Int. Cl.
*C07F 5/02*    (2006.01)

(52) U.S. Cl.
CPC .............. *C07F 5/02* (2013.01); *Y02P 20/582* (2015.11)

(58) Field of Classification Search
CPC ....................................................... C07F 5/02
See application file for complete search history.

(56) References Cited

PUBLICATIONS

Eckert et al. "Molecular diabolos: synthesis of subphthalocyanine-based diboranes" Chemical Communications, 2007, pp. 4104-4106.*

* cited by examiner

*Primary Examiner* — Joseph R Kosack
(74) *Attorney, Agent, or Firm* — Marshall, Gerstein & Borun LLP

(57) ABSTRACT

The disclosure is directed to diboron compounds, related methods of making, and related intermediate boron and diboron compounds used to make the same. The diboron compounds can be used as reagents to prepare chemical intermediates that are used in pharmaceutical, agrochemical, and specialty electronics industries. The disclosed processes and compounds provide simplified synthetic paths that significantly reduce steps, improve scalability, and minimize costs for producing the diboron reagents.

8 Claims, No Drawings

SYNTHETIC METHODS FOR DIBORON REAGENTS AND RELATED COMPOUNDS

CROSS REFERENCE TO RELATED APPLICATION

Priority is claimed to U.S. Provisional Application No. 62/057,780 (filed on Sep. 30, 2014), which is incorporated herein by reference in its entirety.

STATEMENT OF GOVERNMENT INTEREST

None.

BACKGROUND OF THE DISCLOSURE

Field of the Disclosure

The disclosure relates to diboron compounds, which can be used as reagents to prepare chemical intermediates that are used in pharmaceutical, agrochemical, and specialty electronics industries. Such diboron compounds currently retail between about $300/kg to $800/kg, and the expense can be attributed to their complicated synthesis, which has not been significantly improved since the 1960s.

SUMMARY

Diboron reagents are used on metric ton scales for a variety of chemical processes, for example as starting compounds for various pharmaceutical, agrochemical, and specialty electronics compounds. Despite their widespread use, their synthesis involves multiple steps and batch processing, making them costly. The processes and compounds disclosed herein provide simplified syntheses that significantly reduce steps, improve scalability, and minimize costs for producing these diboron reagents.

In one aspect, the disclosure relates to a boron compound (e.g., in pure or substantially pure form (such as at least 90 wt. %, 95 wt. %, 98 wt. %, or 99 wt. % pure), or in admixture with other components) having a structure according to the following Formula I:

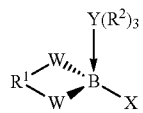

(I)

wherein: (i) the W atoms are independently selected from the group consisting of O and S; (ii) the $R^1$ group is an alkylene group (e.g., linear or branched alkyl or heteroalkyl (e.g., N, O, S-containing) groups with 2, 3, 4, 5, or 6 carbon atoms such as an ethylene or propylene group, for example where the (hetero)alkylene group joins the two W atoms at its terminal ends or at an intermediate location of its chain); (iii) the X atom is selected from the group consisting of Cl, F, Br, I; (iv) the Y atom coordinated to the boron atom (B) is selected from the group consisting of N and P; and (v) the $R^2$ groups are independently selected from the group consisting of an alkyl group and an aryl group (e.g., same or different groups for each of the $R^2$ groups; linear or branched alkyl or heteroalkyl (e.g., N, O, S-containing) groups with 1, 2, 3, 4, 5, or 6 carbon atoms such as methyl, ethyl, propyl, butyl, pentyl, or hexyl; aryl or heteroaryl (e.g., N, O, S-containing) groups with 4, 5, or 6 carbon atoms such as phenyl).

In another aspect, the disclosure relates to a method for forming the boron compound of Formula I, the method comprising: (a) reacting at least one of an alkane diol and an alkane dithiol with a boron trihalide to form a product (e.g., a linear or branched alkyl or heteroalkyl (e.g., N, O, S-containing) diol or dithiol with 2, 3, 4, 5, or 6 carbon atoms and at least 2 hydroxy groups or at least 2 thiol groups such as ethylene glycol or 1,2-ethanedithiol; the product is a dialkoxyboron halide (when using a diol) or a sulfur-equivalent (when using a dithiol); the three halogen atoms of the boron trihalide can be the same or different); and (b) reacting the product of part (a) with at least one of a tri(alkyl and/or aryl) amine and a tri(alkyl and/or aryl) phosphine to form the boron compound according to Formula I (e.g., such as trimethyl amine and triphenylphosphine; the alkyl and aryl groups of the amine and phosphine can be as described in Formula I as $R^2$ group alternatives). In a refinement, the alkane diol is used and comprises ethylene glycol. In a refinement, the boron trihalide comprises boron trichloride. In a refinement, the amine comprises trimethyl amine.

In another aspect, the disclosure relates to a diboron compound (e.g., in pure or substantially pure form (such as at least 90 wt. %, 95 wt. %, 98 wt. %, or 99 wt. % pure), or in admixture with other components) having a structure according to the following Formula II:

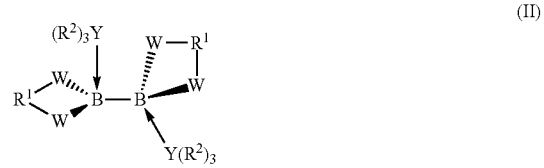

(II)

wherein: (i) the W atoms are independently selected from the group consisting of O and S; (ii) the $R^1$ groups are the same or different alkylene groups (e.g., linear or branched alkyl or heteroalkyl (e.g., N, O, S-containing) groups with 2, 3, 4, 5, or 6 carbon atoms such as an ethylene or propylene group, for example where the (hetero)alkyl group joins the two W atoms at its terminal ends or at an intermediate location of its chain); (iii) the Y atoms coordinated to the boron atoms (B) are independently selected from the group consisting of N and P; and (iv) the $R^2$ groups are independently selected from the group consisting of an alkyl group and an aryl group (e.g., same or different groups each of the $R^2$ groups, linear or branched alkyl or heteroalkyl (e.g., N, O, S-containing) groups with 1, 2, 3, 4, 5, or 6 carbon atoms such as methyl, ethyl, propyl, butyl, pentyl, or hexyl; aryl or heteroaryl (e.g., N, O, S-containing) groups with 4, 5, or 6 carbon atoms such as phenyl).

In another aspect, the disclosure relates to a method for forming a diboron compound, the method comprising: (a) reacting the boron compound of Formula I with a metal to form a diboron compound (e.g., diboron compound of Formula II; metal can be an alkali metal such as Na or K, an alkali earth metal, or other metal to additionally form a metal halide salt byproduct in addition to the diboron compound of Formula II; the metal can be combined with silica or other delivery vehicle for the metal). In a refinement, the metal comprises sodium optionally in combination with silica. In a refinement, the method further comprises forming the boron compound of Formula I according to any of the foregoing methods.

In another aspect, the disclosure relates to a method for forming a tetraalkoxy diboron compound, the method comprising: (a) reacting the diboron compound of Formula II with one or more alkanols having at least one hydroxy group to form the tetraalkoxy diboron compound (e.g., a linear or branched alkyl or heteroalkyl (e.g., N, O, S-containing) diol with 2, 3, 4, 5, 6 and/or up to 10 carbon atoms and 2 hydroxy groups such as pinacol; a linear or branched alkyl or heteroalkyl (e.g., N, O, S-containing) monoalcohol with 1, 2, 3, 4, 5, 6 and/or up to 10 carbon atoms and 1 hydroxy group such as methanol). In a refinement, the one or more alkanols comprises pinacol and the tetraalkoxy diboron compound comprises bis(pinacolato)diboron ($B_2pin_2$). In a refinement, an alkane diol and/or a tri(alkyl and/or aryl) amine as above are further formed as reaction products in part (a) (e.g., where such additional reaction products can be recovered/separated from the tetraalkoxy diboron compound product and/or recycled as reactants for forming the boron compound). In a refinement, the method further comprises forming the diboron compound of Formula II according to any of the foregoing methods (e.g., in a complete process as illustrated in the top pathway of Scheme 3, with or without removal and recycle of byproducts as an initial reactant).

In another aspect, the disclosure relates to boron compound (e.g., in pure or substantially pure form (such as at least 90 wt. %, 95 wt. %, 98 wt. %, or 99 wt. % pure), or in admixture with other components) having a structure according to the following Formula III:

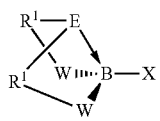

(III)

wherein: (i) the W atoms are independently selected from the group consisting of O and S; (ii) the E group coordinated to the boron atom (B) is selected from the group consisting of an O atom, an S atom, an alkyl amino group, an aryl amino group, an alkyl phosphino group, and an aryl phosphino group (e.g., an amino or phosphino group with a linear or branched alkyl or heteroalkyl (e.g., N, O, S-containing) group with 1, 2, 3, 4, 5, or 6 carbon atoms such as methyl, ethyl, propyl, butyl, pentyl, or hexyl, or an aryl or heteroaryl (e.g., N, O, S-containing) group with 4, 5, or 6 carbon atoms such as phenyl); (iii) the $R^1$ groups are the same or different alkylene groups (e.g., same or different linear or branched alkyl or heteroalkyl (e.g., N, O, S-containing) groups with 2, 3, 4, 5, or 6 carbon atoms such as an ethylene or propylene group, for example where the (hetero)alkylene group joins the W atom and E group at its terminal ends or at an intermediate location of its chain); and (iv) the X atom is selected from the group consisting of Cl, F, Br, I.

In another aspect, the disclosure relates to a method for forming the boron compound of Formula III, the method comprising: (a) reacting a silane compound according to the following Formula IIIA with a boron trihalide to form the boron compound of Formula III (e.g., a boron trihalide where the three halogen atoms are the same or different):

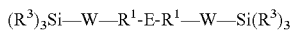

(IIIA)

wherein: (i) the W atoms are independently selected from the group consisting of O and S; (ii) the E group is selected from the group consisting of an O atom, an S atom, an alkyl amino group, an aryl amino group, an alkyl phosphino group, and an aryl phosphino group (e.g., an amino or phosphino group with a linear or branched alkyl or heteroalkyl (e.g., N, O, S-containing) group with 1, 2, 3, 4, 5, or 6 carbon atoms such as methyl, ethyl, propyl, butyl, pentyl, or hexyl, or an aryl or heteroaryl (e.g., N, O, S-containing) group with 4, 5, or 6 carbon atoms such as phenyl); (iii) the $R^1$ groups are the same or different alkylene groups joining the W atoms and the E group (e.g., same or different linear or branched alkyl or heteroalkyl (e.g., N, O, S-containing) groups with 2, 3, 4, 5, or 6 carbon atoms such as an ethylene or propylene group, for example where the (hetero)alkylene group joins the W atom and E group at its terminal ends or at an intermediate location of its chain); and (iv) the $R^3$ groups are independently selected from the group consisting of an alkyl group and an aryl group (e.g., linear or branched alkyl or heteroalkyl (e.g., N, O, S-containing) groups with 1, 2, 3, 4, 5, or 6 carbon atoms such as methyl, ethyl, propyl, butyl, pentyl, or hexyl; aryl or heteroaryl (e.g., N, O, S-containing) groups with 4, 5, or 6 carbon atoms such as phenyl). In a refinement, the E group is an oxygen atom (O). In a refinement, the E group is a methylamino group (NMe). In a refinement, the boron trihalide comprises boron trichloride. In a refinement, part (a) further comprises forming a tri(alkyl and/or aryl)silyl halide (e.g., where such additional reaction product can be recovered/separated from the boron compound product and/or recycled as a reactant for forming the silane compound of Formula IIIA).

In another aspect, the disclosure relates to a diboron compound (e.g., in pure or substantially pure form (such as at least 90 wt. %, 95 wt. %, 98 wt. %, or 99 wt. % pure), or in admixture with other components) having a structure according to the following Formula IV:

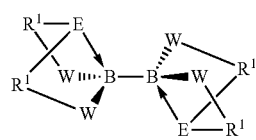

(IV)

wherein: (i) the W atoms are independently selected from the group consisting of O and S; (ii) the E groups coordinated to the boron atom (B) are independently selected from the group consisting of an O atom, an S atom, an alkyl amino group, an aryl amino group, an alkyl phosphino group, and an aryl phosphino group (e.g., an amino or phosphino group with a linear or branched alkyl or heteroalkyl (e.g., N, O, S-containing) group with 1, 2, 3, 4, 5, or 6 carbon atoms such as methyl, ethyl, propyl, butyl, pentyl, or hexyl, or an aryl or heteroaryl (e.g., N, O, S-containing) group with 4, 5, or 6 carbon atoms such as phenyl); and (iii) the $R^1$ groups are the same or different alkylene groups (e.g., same or different linear or branched alkyl or heteroalkyl (e.g., N, O, S-containing) groups with 2, 3, 4, 5, or 6 carbon atoms such as an ethylene or propylene group, for example where the (hetero) alkylene group joins the W atom and E group at its terminal ends or at an intermediate location of its chain).

In another aspect, the disclosure relates to method for forming a diboron compound, the method comprising: (a) reacting the boron compound of Formula III with a metal to form the diboron compound (e.g., an alkali metal such as Na or K, an alkali earth metal, or other metal to additionally form a metal halide salt byproduct in addition to the diboron compound; the metal can be combined with silica or other delivery vehicle for the metal). In a refinement, the metal comprises sodium optionally in combination with silica. In a refinement, the method comprises forming the boron compound of Formula III according to any of the foregoing disclosed methods.

In another aspect, the disclosure relates to a method for forming a tetraalkoxy diboron compound, the method comprising: (a) reacting the diboron compound of Formula IV with one or more alkanols having at least one hydroxy group to form the tetraalkoxy diboron compound (e.g., a linear or branched alkyl or heteroalkyl (e.g., N, O, S-containing) diol with 2, 3, 4, 5, 6 and/or up to 10 carbon atoms and 2 hydroxy groups such as pinacol; a linear or branched alkyl or heteroalkyl (e.g., N, O, S-containing) monoalcohol with 1, 2, 3, 4, 5, 6 and/or up to 10 carbon atoms and 1 hydroxy group such as methanol). In a refinement, the one or more alkanols comprises pinacol and the tetraalkoxy diboron compound comprises bis(pinacolato)diboron ($B_2pin_2$). In a refinement, a diol analog of the compound according to Formula IIIA as is further formed as a reaction product in part (a) (e.g., where such additional reaction products can be recovered/separated from the tetraalkoxy diboron compound product and/or recycled as reactants for forming the compound according to Formula IIIA). In a refinement, the method further comprises forming the diboron compound of Formula IV according to the method of any of the foregoing embodiments (e.g., in a complete process as illustrated in the bottom pathway of Scheme 3, with or without removal and recycle of byproducts as an initial reactant).

In another aspect, the method for forming a diboron compound, the method comprising: (a) reacting a 4-coordinate boron compound with a metal (e.g., an alkali metal such as Na or K, an alkali earth metal, or other metal to additionally form a metal halide salt byproduct; the metal can be combined with silica or other delivery vehicle for the metal) under suitable conditions to form a 4-coordinate diboron compound, wherein: (i) the 4-coordinate boron compound comprises (A) a boron atom, (B) one halogen atom (e.g., F, Cl, Br, I) covalently bonded to the boron atom, (C) two same or different heteroatoms selected from the group consisting of N, O, P, and S covalently bonded to the boron atom, and (D) one heteroatom selected from the group consisting of N, O, P, and S coordinately covalently bonded to the boron atom (e.g., where the three heteroatoms covalently bonded or coordinately covalently bonded to the boron atom can be the same or different from each other, and/or the three heteroatoms can be bonded to any other suitable (hetero) alkyl and/or (hetero)aryl groups are described above); and, (ii) the 4-coordinate diboron compound comprises an adduct of two 4-coordinate boron compound molecules joined by a B—B covalent bond after elimination of their halogen atoms (e.g., each B atom having 3 covalent bonds and 1 coordinate covalent bond as above with each B-halogen covalent bond replaced by the mutual B—B covalent bond). In a refinement, the method further comprises (b) reacting the 4-coordinate diboron compound with one or more alkanols having at least one hydroxy group to form a tetraalkoxy diboron compound (e.g., a linear or branched alkyl or heteroalkyl (e.g., N, O, S-containing) diol with 2, 3, 4, 5, 6 and/or up to 10 carbon atoms and 2 hydroxy groups such as pinacol; a linear or branched alkyl or heteroalkyl (e.g., N, O, S-containing) monoalcohol with 1, 2, 3, 4, 5, 6 and/or up to 10 carbon atoms and 1 hydroxy group such as methanol).

While the disclosed compounds, methods and compositions are susceptible of embodiments in various forms, specific embodiments of the disclosure are illustrated (and will hereafter be described) with the understanding that the disclosure is intended to be illustrative, and is not intended to limit the claims to the specific embodiments described and illustrated herein.

DETAILED DESCRIPTION

A current synthesis of the tetraalkoxydiboron reagent $B_2pin_2$ (bis(pinacolato)diboron, where "pin" represents the reaction product of pinacol with boron as illustrated) is outlined in Scheme 1. While $BCl_3$ is a cheap source of boron, the direct route to $B_2pin_2$ from ClBpin (1, Scheme 1) fails because the product, which contains 3-coordinate boron atoms, also reacts with Na. While related compounds have been reduced to make B—B bonds, these reactions require Na/Hg amalgams for success. The large volumes of mercury that would be required produce diboron compounds on industrial scales make this route infeasible.

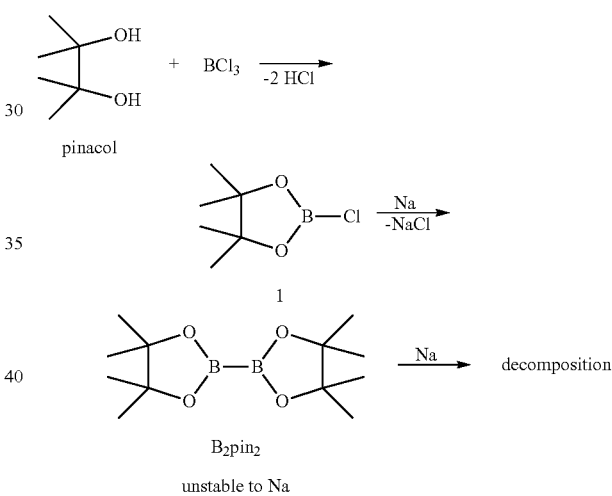

Scheme 1

The current route to $B_2pin_2$ requires preparation of boron nitrogen compound 2 from $BCl_3$ and dimethylamine. Compound 2 is then reduced to form boron-boron bonded compound 3. Because compound 3 is unreactive, it must be converted to $B_2pin_2$ in a reaction with pinacol and 8 equivalents of hydrochloric acid. The 4-step process for preparing $B_2pin_2$ from $BCl_3$ generates 8 equivalents of $NH_2Me_2Cl$ waste for every molecule of $B_2pin_2$ produced. Each step requires careful purification of products, and the toxic amine waste stream must be remediated. Under best practices, the yields of $B_2pin_2$ are limited to about 30%.

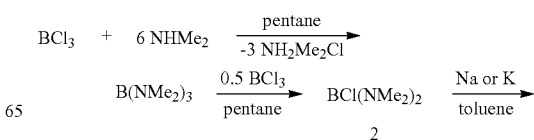

Scheme 2

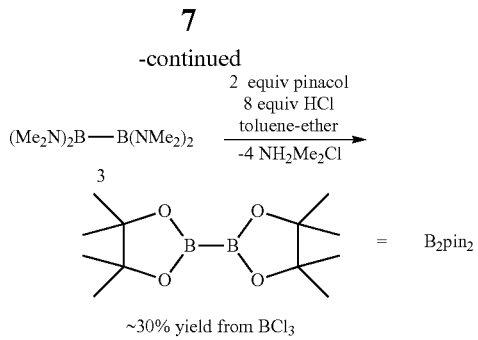

~30% yield from BCl₃

The present disclosure uses dialkoxyboron halides that are stabilized by nitrogen or oxygen donors (Scheme 3, compounds 4-6). Boron-boron bond formation is accomplished by reduction with an alkali metal or alkali metal-silica such as Na or Na-silica, a safe source of Na with improved chemical reactivity. Because the boron atoms in compounds 7-9 are four-coordinate, they will be unreactive towards Na, and unwanted side reactions will be avoided. Compounds 7-9 can be converted to $B_2pin_2$ in straightforward fashion. This also will allow other diboron diolate (or alkanolate) reagents to be formed (e.g., by reacting compounds 7-9 or similar analogs with other alkyl or aryl alcohols, diols, triols, or higher polyols other than pinacol as illustrated). The sequence in Scheme 3 uses intermediates that are crystalline solids, which simplifies purifications. Intermediates 5 and 6 are prepared from cheap diols that can be recycled. Lastly, the route in Scheme 3 minimizes, or eliminates, the generation of ammonium salts, which will significantly reduce waste disposal costs.

wherein: (i) either or both of the oxygen atoms (O) in Formula 1 may be replaced with sulfur (S) atoms; (ii) the $O_2$ ethylene group joining the two oxygen atoms (O) in Formula 1 alternatively may be replaced with an alkyl group (e.g., linear or branched alkyl or heteroalkyl (e.g., N, O, S-containing) groups with 2, 3, 4, 5, or 6 carbon atoms such as an ethylene or propylene group, for example where the (hetero) alkyl group joins the two oxygen atoms at its terminal ends or at an intermediate location of its chain); (iii) the chlorine atom (Cl) in Formula 1 may be replaced with a different halogen (e.g., F, Br, I); (iv) the nitrogen atom (N) coordinated to the boron atom (B) in Formula 1 may be replaced with a phosphorous (P) atom; and (v) any or all of the methyl groups (Me) in Formula 1 may be replaced with an alkyl group or an aryl group, which may be the same or different (e.g., linear or branched alkyl or heteroalkyl (e.g., N, O, S-containing) groups with 1, 2, 3, 4, 5, or 6 carbon atoms such as methyl, ethyl, propyl, butyl, pentyl, or hexyl; aryl or heteroaryl (e.g., N, O, S-containing) groups with 4, 5, or 6 carbon atoms such as phenyl).

2. method for forming the boron compound of paragraph 1, the method comprising: (a) reacting an alkane diol with a boron trihalide to form a dialkoxyboron halide (e.g., a linear

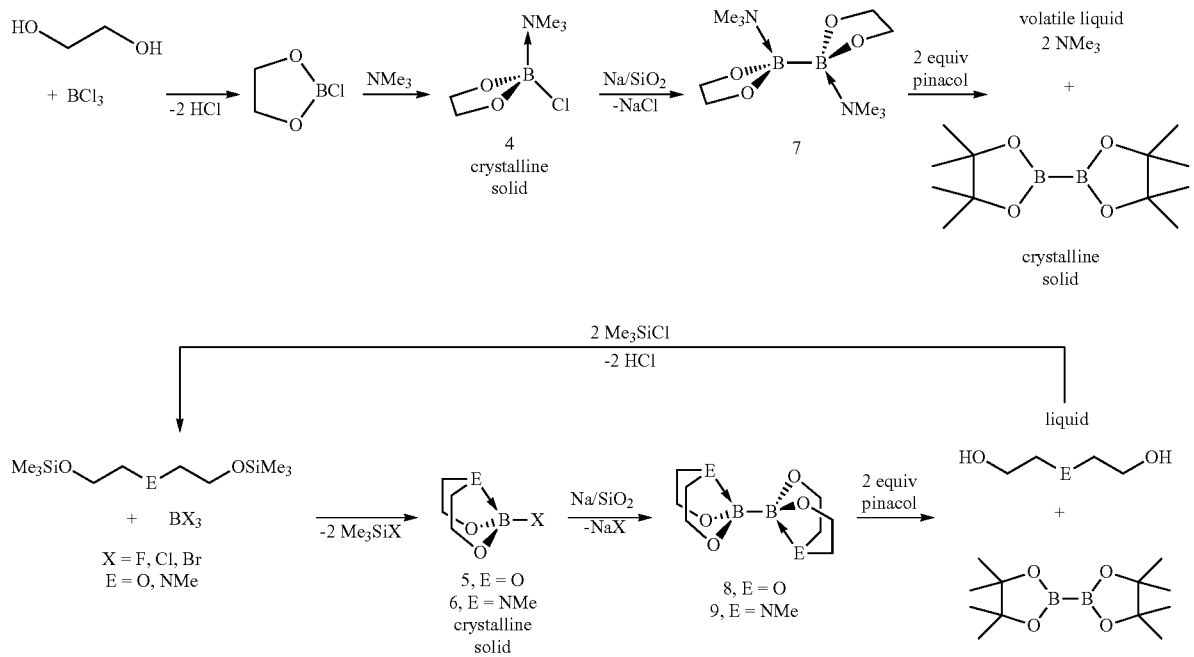

Various aspects of the disclosure are provided by the following numbered paragraphs.

1. A boron compound (e.g., in pure or substantially pure form (such as at least 90 wt. %, 95 wt. %, 98 wt. %, or 99 wt. % pure), or in admixture with other components) having a structure according to the following Formula 1:

or branched alkyl or heteroalkyl (e.g., N, O, S-containing) diol with 2, 3, 4, 5, or 6 carbon atoms and at least 2 hydroxy groups such as ethylene glycol; a boron trihalide where the three halogen atoms are the same or different; and (b) reacting the dialkoxyboron halide with a tri(alkyl and/or aryl) amine to form the boron compound of paragraph 1

(e.g., where the alkyl and aryl groups of the amine can be as described in paragraph 1 as methyl group alternatives).

3. The method of paragraph 2, wherein the alkane diol comprises ethylene glycol.

4. The method of paragraph 2, wherein the boron trihalide comprises boron trichloride.

5. The method of paragraph 2, wherein the amine comprises trimethyl amine.

6. The method of paragraph 2, wherein the alkane diol alternatively may be replaced by or combined with an alkane dithiol (e.g., a thiol analog of the various alkane diols, such as 1,2-ethanedithiol).

7. The method of paragraph 2, wherein the tri(alkyl and/or aryl) amine alternatively may be replaced by or combined with a tri(alkyl and/or aryl) phosphine (e.g., a phosphine analog of the various amines, such as triphenylphosphine).

8. A diboron compound (e.g., in pure or substantially pure form (such as at least 90 wt. %, 95 wt. %, 98 wt. %, or 99 wt. % pure), or in admixture with other components) having a structure according to the following Formula 2:

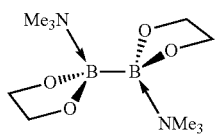

(2)

wherein: (i) any or all of the oxygen atoms (O) in Formula 2 may be replaced with sulfur (S) atoms; (ii) either or both of the $O_2$ ethylene groups joining two oxygen atoms (O) in Formula 2 alternatively may be replaced with an alkyl group (e.g., linear or branched alkyl or heteroalkyl (e.g., N, O, S-containing) groups with 2, 3, 4, 5, or 6 carbon atoms such as an ethylene or propylene group, for example where the (hetero)alkyl group joins the two oxygen atoms at its terminal ends or at an intermediate location of its chain); (iii) either or both of the nitrogen atoms (N) coordinated to the boron atom (B) in Formula 2 may be replaced with a phosphorous (P) atom; and (iv) any or all of the methyl groups (Me) in Formula 2 may be replaced with an alkyl group or an aryl group, which may be the same or different (e.g., linear or branched alkyl or heteroalkyl (e.g., N, O, S-containing) groups with 1, 2, 3, 4, 5, or 6 carbon atoms such as methyl, ethyl, propyl, butyl, pentyl, or hexyl; aryl or heteroaryl (e.g., N, O, S-containing) groups with 4, 5, or 6 carbon atoms such as phenyl).

9. A method for forming the diboron compound of paragraph 8, the method comprising: (a) reacting the boron compound of paragraph 1 with a metal to form the diboron compound of paragraph 8 (e.g., an alkali metal such as Na or K, an alkali earth metal, or other metal to additionally form a metal halide salt byproduct in addition to the diboron compound of paragraph 8; the metal can be combined with silica or other delivery vehicle for the metal).

10. The method of paragraph 9, wherein the metal comprises sodium optionally in combination with silica.

11. The method of paragraph 9, further comprising forming the boron compound of paragraph 1 according to the method of any of paragraphs 2 to 7.

12. A method for forming a tetraalkoxy diboron compound, the method comprising: (a) reacting the diboron compound of paragraph 8 with one or more alkanols having at least one hydroxy group to form the tetraalkoxy diboron compound (e.g., a linear or branched alkyl or heteroalkyl (e.g., N, O, S-containing) diol with 2, 3, 4, 5, 6 and/or up to 10 carbon atoms and 2 hydroxy groups such as pinacol; a linear or branched alkyl or heteroalkyl (e.g., N, O, S-containing) monoalcohol with 1, 2, 3, 4, 5, 6 and/or up to 10 carbon atoms and 1 hydroxy group such as methanol).

13. The method of paragraph 12, wherein the one or more alkanols comprises pinacol and the tetraalkoxy diboron compound comprises bis(pinacolato)diboron ($B_2pin_2$).

14. The method of paragraph 12, wherein an alkane diol and/or a tri(alkyl and/or aryl) amine as recited in paragraph 2 are further formed as reaction products in part (a) (e.g., where such additional reaction products can be recovered/separated from the tetraalkoxy diboron compound product and/or recycled as reactants for forming the boron compound).

15. The method of paragraph 12, further comprising forming the diboron compound of paragraph 8 according to the method of any of paragraphs 9 to 11 (e.g., in a complete process as illustrated in the top pathway of Scheme 3, with or without removal and recycle of byproducts as an initial reactant).

16. A boron compound (e.g., in pure or substantially pure form (such as at least 90 wt. %, 95 wt. %, 98 wt. %, or 99 wt. % pure), or in admixture with other components) having a structure according to the following Formula 3:

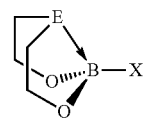

(3)

wherein: (i) either or both of the oxygen atoms (O) in Formula 3 may be replaced with sulfur (S) atoms; (ii) the E group coordinated to the boron atom (B) in Formula 3 may be an oxygen atom (O), a sulfur atom (S), an alkyl or aryl amino group, or an alkyl or aryl phosphino group (e.g., an amino or phosphino group with a linear or branched alkyl or heteroalkyl (e.g., N, O, S-containing) group with 1, 2, 3, 4, 5, or 6 carbon atoms such as methyl, ethyl, propyl, butyl, pentyl, or hexyl, or an aryl or heteroaryl (e.g., N, O, S-containing) group with 4, 5, or 6 carbon atoms such as phenyl); (iii) either or both of the $O_2$ ethylene groups joining the oxygen atoms (O) and E group in Formula 3 alternatively may be replaced with an alkyl group (e.g., same or different linear or branched alkyl or heteroalkyl (e.g., N, O, S-containing) groups with 2, 3, 4, 5, or 6 carbon atoms such as an ethylene or propylene group, for example where the (hetero) alkyl group joins the oxygen atom and E group at its terminal ends or at an intermediate location of its chain); and (iv) the X group in Formula 3 is a halogen (e.g., F, Cl, Br, I).

17. A method for forming the boron compound of paragraph 16, the method comprising: (a) reacting a silane compound according to the following Formula 3A with a boron trihalide to form the boron compound of paragraph 16 (e.g., a boron trihalide where the three halogen atoms are the same or different):

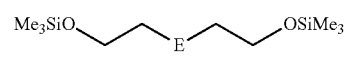

(3A)

wherein: (i) either or both of the oxygen atoms (O) in Formula 3A may be replaced with sulfur (S) atoms; (ii) the E group in Formula 3A may be an oxygen atom (O), a sulfur atom (S), an alkyl or aryl amino group, or an alkyl or aryl phosphino group (e.g., an amino or phosphino group with a linear or branched alkyl or heteroalkyl (e.g., N, O, S-containing) group with 1, 2, 3, 4, 5, or 6 carbon atoms such as methyl, ethyl, propyl, butyl, pentyl, or hexyl, or an aryl or heteroaryl (e.g., N, O, S-containing) group with 4, 5, or 6 carbon atoms such as phenyl); (iii) the $O_2$ ethylene groups joining the oxygen atoms (O) and E group in Formula 3A alternatively may be replaced with an alkyl group (e.g., same or different linear or branched alkyl or heteroalkyl (e.g., N, O, S-containing) groups with 2, 3, 4, 5, or 6 carbon atoms such as an ethylene or propylene group, for example where the (hetero)alkyl group joins the oxygen atom and E group at its terminal ends or at an intermediate location of its chain); and (iv) any or all of the methyl groups (Me) in Formula 3A may be replaced with an alkyl group or an aryl group, which may be the same or different (e.g., linear or branched alkyl or heteroalkyl (e.g., N, O, S-containing) groups with 1, 2, 3, 4, 5, or 6 carbon atoms such as methyl, ethyl, propyl, butyl, pentyl, or hexyl; aryl or heteroaryl (e.g., N, O, S-containing) groups with 4, 5, or 6 carbon atoms such as phenyl).

18. The method of paragraph 17, wherein the E group is an oxygen atom (O).

19. The method of paragraph 17, wherein the E group is a methylamino group (NMe).

20. The method of paragraph 17, wherein the boron trihalide comprises boron trichloride.

21. The method of paragraph 17, wherein part (a) further comprises forming a tri(alkyl and/or aryl)silyl halide (e.g., where such additional reaction product can be recovered/separated from the boron compound product and/or recycled as a reactant for forming the silane compound of Formula 3A).

22. A diboron compound (e.g., in pure or substantially pure form (such as at least 90 wt. %, 95 wt. %, 98 wt. %, or 99 wt. % pure), or in admixture with other components) having a structure according to the following Formula 4:

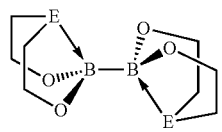

(4)

wherein: (i) any or all of the oxygen atoms (O) in Formula 4 may be replaced with sulfur (S) atoms; (ii) either or both of the E groups coordinated to the boron atom (B) in Formula 4 may be an oxygen atom (O), a sulfur atom (S), an alkyl or aryl amino group, or an alkyl or aryl phosphino group (e.g., an amino or phosphino group with a linear or branched alkyl or heteroalkyl (e.g., N, O, S-containing) group with 1, 2, 3, 4, 5, or 6 carbon atoms such as methyl, ethyl, propyl, butyl, pentyl, or hexyl, or an aryl or heteroaryl (e.g., N, O, S-containing) group with 4, 5, or 6 carbon atoms such as phenyl); and (iii) any or all of the $O_2$ ethylene groups joining the oxygen atoms (O) and E group in Formula 4 alternatively may be replaced with an alkyl group (e.g., same or different linear or branched alkyl or heteroalkyl (e.g., N, O, S-containing) groups with 2, 3, 4, 5, or 6 carbon atoms such as an ethylene or propylene group, for example where the (hetero)alkyl group joins the oxygen atom and E group at its terminal ends or at an intermediate location of its chain).

23. A method for forming the diboron compound of paragraph 22, the method comprising: (a) reacting the boron compound of paragraph 16 with a metal to form the diboron compound of paragraph 22 (e.g., an alkali metal such as Na or K, an alkali earth metal, or other metal to additionally form a metal halide salt byproduct in addition to the diboron compound of paragraph 22; the metal can be combined with silica or other delivery vehicle for the metal).

24. The method of paragraph 23, wherein the metal comprises sodium optionally in combination with silica.

25. The method of paragraph 23, further comprising forming the boron compound of paragraph 16 according to the method of any of paragraphs 17 to 21.

26. A method for forming a tetraalkoxy diboron compound, the method comprising: (a) reacting the diboron compound of paragraph 22 with one or more alkanols having at least one hydroxy group to form the tetraalkoxy diboron compound (e.g., a linear or branched alkyl or heteroalkyl (e.g., N, O, S-containing) diol with 2, 3, 4, 5, 6 and/or up to 10 carbon atoms and 2 hydroxy groups such as pinacol; a linear or branched alkyl or heteroalkyl (e.g., N, O, S-containing) monoalcohol with 1, 2, 3, 4, 5, 6 and/or up to 10 carbon atoms and 1 hydroxy group such as methanol).

27. The method of paragraph 26, wherein the one or more alkanols comprises pinacol and the tetraalkoxy diboron compound comprises bis(pinacolato)diboron ($B_2pin_2$).

28. The method of paragraph 26, wherein a diol analog of the compound according to Formula 3A as recited in paragraph 17 is further formed as a reaction product in part (a) (e.g., where such additional reaction products can be recovered/separated from the tetraalkoxy diboron compound product and/or recycled as reactants for forming the compound according to Formula 3A).

29. The method of paragraph 26, further comprising forming the diboron compound of paragraph 16 according to the method of any of paragraphs to 17 to 21 (e.g., in a complete process as illustrated in the bottom pathway of Scheme 3, with or without removal and recycle of byproducts as an initial reactant).

30. A method for forming a diboron compound, the method comprising: (a) reacting a 4-coordinate boron compound with a metal (e.g., an alkali metal such as Na or K, an alkali earth metal, or other metal to additionally form a metal halide salt byproduct; the metal can be combined with silica or other delivery vehicle for the metal) under suitable conditions to form a 4-coordinate diboron compound, wherein: (i) the 4-coordinate boron compound comprises (A) a boron atom, (B) one halogen atom (e.g., F, Cl, Br, I) covalently bonded to the boron atom, (C) two same or different heteroatoms selected from the group consisting of N, O, P, and S covalently bonded to the boron atom, and (D) one heteroatom selected from the group consisting of N, O, P, and S coordinately covalently bonded to the boron atom (e.g., where the three heteroatoms covalently bonded or coordinately covalently bonded to the boron atom can be the same or different from each other, and/or the three heteroatoms can be bonded to any other suitable (hetero)alkyl and/or (hetero)aryl groups are described above); and, (ii) the 4-coordinate diboron compound comprises an adduct of two 4-coordinate boron compound molecules joined by a B—B covalent bond after elimination of their halogen atoms (e.g., each B atom having 3 covalent bonds and 1 coordinate covalent bond as above with each B-halogen covalent bond replaced by the mutual B—B covalent bond).

31. The method of paragraph 30, further comprising (b) reacting the 4-coordinate diboron compound with one or more alkanols having at least one hydroxy group to form a tetraalkoxy diboron compound (e.g., a linear or branched alkyl or heteroalkyl (e.g., N, O, S-containing) diol with 2, 3, 4, 5, 6 and/or up to 10 carbon atoms and 2 hydroxy groups such as pinacol; a linear or branched alkyl or heteroalkyl (e.g., N, O, S-containing) monoalcohol with 1, 2, 3, 4, 5, 6 and/or up to 10 carbon atoms and 1 hydroxy group such as methanol).

Because other modifications and changes varied to fit particular operating requirements and environments will be apparent to those skilled in the art, the disclosure is not considered limited to the example chosen for purposes of illustration, and covers all changes and modifications which do not constitute departures from the true spirit and scope of this disclosure.

Accordingly, the foregoing description is given for clearness of understanding only, and no unnecessary limitations should be understood therefrom, as modifications within the scope of the disclosure may be apparent to those having ordinary skill in the art.

All patents, patent applications, government publications, government regulations, and literature references cited in this specification are hereby incorporated herein by reference in their entirety. In case of conflict, the present description, including definitions, will control.

Throughout the specification, where the compounds, compositions, methods, and processes are described as including components, steps, or materials, it is contemplated that the compositions, processes, or apparatus can also comprise, consist essentially of, or consist of, any combination of the recited components or materials, unless described otherwise. Component concentrations can be expressed in terms of weight concentrations, unless specifically indicated otherwise. Combinations of components are contemplated to include homogeneous and/or heterogeneous mixtures, as would be understood by a person of ordinary skill in the art in view of the foregoing disclosure.

What is claimed is:

1. A method for forming a diboron compound, the method comprising:
    (a) reacting a 4-coordinate boron compound with a metal under suitable conditions to form a 4-coordinate diboron compound, wherein:
        (i) the 4-coordinate boron compound comprises (A) a boron atom, (B) one halogen atom covalently bonded to the boron atom, (C) two same or different heteroatoms selected from the group consisting of N, O, P, and S covalently bonded to the boron atom, and (D) one heteroatom selected from the group consisting of N, O, P, and S coordinately covalently bonded to the boron atom;
        (ii) the 4-coordinate diboron compound comprises an adduct of two of the 4-coordinate boron compound molecules joined by a B—B covalent bond after elimination of their halogen atoms; and,
        (iii) the 4-coordinate boron compound has a structure according to the following Formula I:

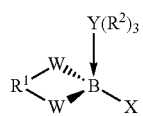

(I)

wherein:
    (i) the W atoms are independently selected from the group consisting of O and S;
    (ii) the $R^1$ group is an alkylene group;
    (iii) the X atom is selected from the group consisting of Cl, F, Br, and I;
    (iv) the Y atom coordinated to the boron atom (B) is selected from the group consisting of N and P; and
    (v) the $R^2$ groups are independently selected from the group consisting of an alkyl group and an aryl group.

2. The method of claim 1, further comprising forming the 4-coordinate boron compound according to Formula I by:
    (a) reacting at least one of an alkane diol and an alkane dithiol with a boron trihalide to form a product; and
    (b) reacting the product of part (a) with at least one of a tri(alkyl and/or aryl) amine and a tri(alkyl and/or aryl) phosphine to form the boron compound according to Formula I.

3. The method of claim 1, wherein the 4-coordinate diboron compound has a structure according to the following Formula II:

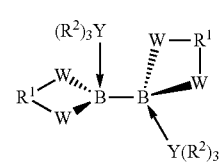

(II)

wherein:
    (i) the W atoms are independently selected from the group consisting of O and S;
    (ii) the $R^1$ groups are the same or different alkylene groups;
    (iii) the Y atoms coordinated to the boron atoms (B) are independently selected from the group consisting of N and P; and
    (iv) the $R^2$ groups are independently selected from the group consisting of an alkyl group and an aryl group.

4. A method for forming a tetraalkoxy diboron compound, the method comprising:
    (a) reacting the diboron compound of claim 3 with one or more alkanols having at least one hydroxy group to form the tetraalkoxy diboron compound.

5. A method for forming a diboron compound, the method comprising:
    (a) reacting a 4-coordinate boron compound with a metal under suitable conditions to form a 4-coordinate diboron compound, wherein:
        (i) the 4-coordinate boron compound comprises (A) a boron atom, (B) one halogen atom covalently bonded to the boron atom, (C) two same or different heteroatoms selected from the group consisting of N, O, P, and S covalently bonded to the boron atom, and (D) one heteroatom selected from the group consisting of N, O, P, and S coordinately covalently bonded to the boron atom;
        (ii) the 4-coordinate diboron compound comprises an adduct of two of the 4-coordinate boron compound molecules joined by a B—B covalent bond after elimination of their halogen atoms; and,
        (iii) the 4-coordinate boron compound has a structure according to the following Formula III:

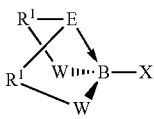

(III)

wherein:
(i) the W atoms are independently selected from the group consisting of O and S;
(ii) the E group coordinated to the boron atom (B) is selected from the group consisting of an O atom, an S atom, an alkyl amino group, an aryl amino group, an alkyl phosphino group, and an aryl phosphino group;
(iii) the $R^1$ groups are the same or different alkylene groups; and
(iv) the X atom is selected from the group consisting of Cl, F, Br, and I.

6. The method of claim 5, further comprising forming the 4-coordinate boron compound according to Formula III by:
(a) reacting a silane compound according to the following Formula IIIA with a boron trihalide to form the boron compound of Formula III:

$$(R^3)_3Si-W-R^1\text{-}E\text{-}R^1-W-Si(R^3)_3 \quad \text{(IIIA)}$$

wherein:
(i) the W atoms are independently selected from the group consisting of O and S;
(ii) the E group is selected from the group consisting of an O atom, an S atom, an alkyl amino group, an aryl amino group, an alkyl phosphino group, and an aryl phosphino group;
(iii) the $R^1$ groups are the same or different alkylene groups joining the W atoms and the E group; and
(iv) the $R^3$ groups are independently selected from the group consisting of an alkyl group and an aryl group.

7. The method of claim 5, wherein the 4-coordinate diboron compound has a structure according to the following Formula IV:

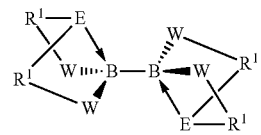

(IV)

wherein:
(i) the W atoms are independently selected from the group consisting of O and S;
(ii) the E groups coordinated to the boron atom (B) are independently selected from the group consisting of an O atom, an S atom, an alkyl amino group, an aryl amino group, an alkyl phosphino group, and an aryl phosphino group; and
(iii) the $R^1$ groups are the same or different alkylene groups.

8. A method for forming a tetraalkoxy diboron compound, the method comprising:
(a) reacting the diboron compound of claim 7 with one or more alkanols having at least one hydroxy group to form the tetraalkoxy diboron compound.

* * * * *